United States Patent [19]

Mais et al.

[11] Patent Number: 5,801,284
[45] Date of Patent: Sep. 1, 1998

[54] HYDROGENATION OF HALONITROAROMATIC COMPOUNDS

[75] Inventors: Franz-Josef Mais, Düsseldorf; Klaus-Christian Paetz, Burscheid; Helmut Fiege, Leverkusen; Heinz Ulrich Blank, Odenthal; Dieter Brueck, Bonn; Wolf Mehl, Köln, all of Germany

[73] Assignee: Bayer Aktiengesellschaft, Leverkusen, Germany

[21] Appl. No.: 795,985

[22] Filed: Feb. 5, 1997

[30] Foreign Application Priority Data

Feb. 12, 1996 [DE] Germany .......................... 196 04 988.1

[51] Int. Cl.$^6$ .................................................. C07C 209/36
[52] U.S. Cl. ................. 564/417; 548/368.4; 548/368.7; 564/155; 564/164; 564/168; 560/110
[58] Field of Search ...................... 564/417, 155, 564/164, 168; 548/368.4, 368.7; 560/110

[56] References Cited

U.S. PATENT DOCUMENTS 3,350,450 10/1967 Dovell et al. .
3,761,425  9/1973 Baessler et al. .
3,929,891 12/1975 Habig et al. .
4,287,365  9/1981 Becker et al. .
4,443,536  4/1984 Lestina .

FOREIGN PATENT DOCUMENTS 0 073 636    3/1983  European Pat. Off. .
0 647 472 A1 4/1995  European Pat. Off. .
27 13 374 A1 9/1978  Germany .
   159 875    4/1983  Germany .
   53-73528   6/1978  Japan .
WO 89/07096  8/1989  WIPO .

OTHER PUBLICATIONS

Database WPI, AN 78–56085A, Abstract of JP 53 073 528 (1978).
Chemical Abstracts, vol. 99, abstract No. 212267, abstract of DD 159 875 (1983).
H. Adkins et al, Or.Synthesis, Col. vol. II, 180 (1955).

Primary Examiner—Brian M. Burn
Attorney, Agent, or Firm—Sprung Kramer Schaefer & Briscoe

[57] ABSTRACT

Process for preparing haloaromatic amines by catalytic hydrogenation of the corresponding halonitroaromatic compounds, characterized in that iron-containing Raney nickel is used as catalyst, where the haloaromatic amines prepared can be used for the synthesis of photographic couplers which are useful in photographic emulsions or elements.

8 Claims, No Drawings

HYDROGENATION OF HALONITROAROMATIC COMPOUNDS

The invention relates to a process for preparing haloaromatic amines by catalytic hydrogenation of the corresponding nitro compounds using iron-containing Raney nickel.

Problems which occur in the preparation of haloaromatic amines by catalytic hydrogenation from the corresponding nitro compounds are, for example, the insufficient catalytic activity or selectivity which leads to incomplete reaction of the starting material used or to substantial amounts of undesired dehalogenation products as by-products. Contamination by by-products and possibly unreacted starting material makes additional purification steps necessary, which is generally associated with a high additional cost.

High purity is required, in particular, of the haloaromatic amines used for preparing pharmaceuticals and photographic chemicals.

In the prior art, numerous routes have already been examined for preparing haloaromatic amines with retention of the halogen atom from the corresponding nitro compound by means of catalytic hydrogenation.

For this purpose, for example, sulphides of platinum, rhodium, ruthenium or cobalt (U.S. Pat. No. 3,350,450) or sulphided or sulphited noble metal/carbon catalysts have been used (U.S. Pat. No. 3,761,425, U.S. Pat. No. 3,929,891). In WO-A-89/07096, the dehalogenation of such compounds is prevented by use of a chromium-containing Raney cobalt catalyst, but complicated process steps or parameters lead to unsatisfactory space—time yields. In DD-A-159 875, haloaromatic amines, inter alia, are obtained by catalytic hydrogenation of the corresponding nitro compounds using Raney nickel as catalyst. However, in this procedure the proportion of dehalogenation products is still very high.

A process has now been found for preparing haloaromatic amines by catalytic hydrogenation of the corresponding halonitroaromatic compounds, which process is characterized in that iron-containing Raney nickel is used as catalyst.

For the purposes of this application, a haloaromatic amine is a compound which bears at least one amino group on the carbon atoms of an aromatic carbocyclic ring and bears at least one halogen atom on the carbon atoms of the same ring or on the carbon atoms of other carbocyclic aromatic rings. For the purposes of this application, a halonitroaromatic compound is the corresponding nitro compound.

Suitable carbocyclic aromatic rings are, in particular, benzene or naphthalene rings which may be further substituted.

Preferred halonitroaromatic compounds are nitroaromatic bromides, iodides and chlorides. Particular preference is given to nitroaromatic chlorides.

The halonitroaromatic compounds preferably used in the process of the invention or the corresponding haloaromatic amines thus obtained correspond to the formulae (I) or (II)

where

A is an unsubstituted or substituted aromatic radical to which the $NO_2$ group in formula (I) or the $NH_2$ group in formula (II) is bonded via a ring carbon atom of an aromatic ring and where at least one ring carbon atom of an aromatic ring of the radical A is substituted by at least one halogen atom, in particular chlorine.

The aromatic radical A can bear further substituents such as hydroxy, alkyl, alkoxy, aryloxy, aryl, formyl, alkanoyl, cycloalkanoyl, aroyl, alkanoyloxy, cycloalkanoyloxy, aroyloxy, alkylsulphonyl, cycloalkylsulphonyl, arylsulphonyl, alkanoylamino, cycloalkanoylamino, aroylamino, alkylsulphonamido, cycloalkylsulphonamido, arylsulphonamido, alkoxycarbonyl, cycloalkoxycarbonyl, aryloxycarbonyl, carbamoyl, sulphamoyl, alkyl-, aryl- or heterocyclyl-aminocarbonyl or -carbonylamino and substituted amino.

The alkyl groups in the list of the abovementioned substituents can be unbranched or branched, unsubstituted or substituted $C_1$–$C_{20}$-alkyl groups. Examples of such alkyl groups are: methyl, ethyl, propyl, 2-methoxypropyl, 1,1-dimethylpropyl, hexyl, octyl, 2-ethylhexyl, decyl, dodecyl, hexadecyl, etc.

Preferred cycloalkyl groups are unsubstituted or substituted $C_5$–$C_7$-cycloalkyls such as cyclopentyl, cyclohexyl, cycloheptyl, etc. The aryl radicals are preferably carbocyclic, unsubstituted or substituted $C_8$–$C_{10}$-aromatics such as phenyl or naphthyl. Carbamoyl or sulphamoyl groups can be unsubstituted or substituted, with possible substituents being alkyl, cycloalkyl, and aryl. The substituted amino groups can bear one or two alkyl, cycloalkyl, aryl or heterocyclic radicals.

Particularly preferred substituents of the aromatic radical A are the following:

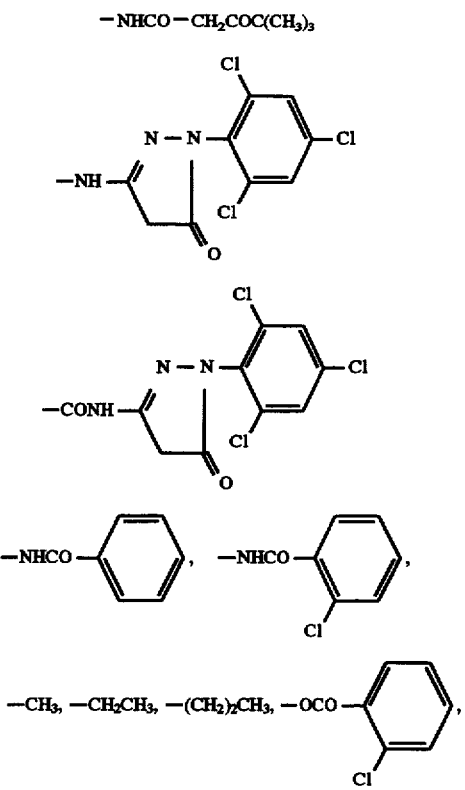

The aromatic radical is preferably an unsubstituted or substituted benzene or naphthalene radical, in particular a benzene radical.

On the aromatic ring on which the $NO_2$ group is located, the aromatic radical A preferably bears one or two of the abovementioned substituents in addition to any halogen atom(s) which may be present. An example of an aromatic radical A containing two halogen atoms is

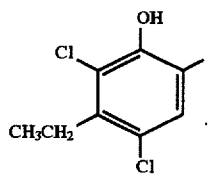

Preferred halonitroaromatic compounds of the formula I correspond to the formula Ia, Ib or Ic and preferred haloaromatic amines of the formula II correspond to the formula IIa, IIb or IIc,

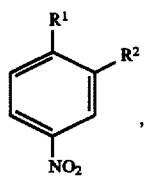 (Ia)

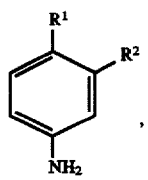 (IIa)

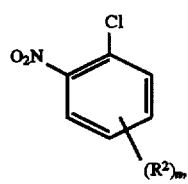 (Ib)

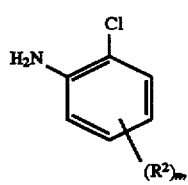 (IIb)

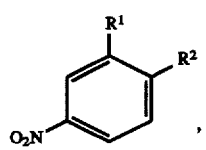 (Ic)

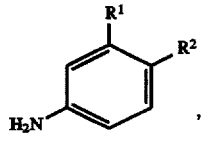 (IIc)

where $R^1$ represents hydrogen or chlorine, n represents 1 or 2 and $R^2$ can be as defined for the possible substituents for A, where, when n=2, $R^2$ can also have different meanings.

Particularly preferred radicals $R^2$ are

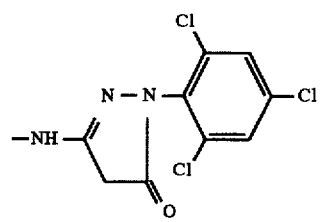

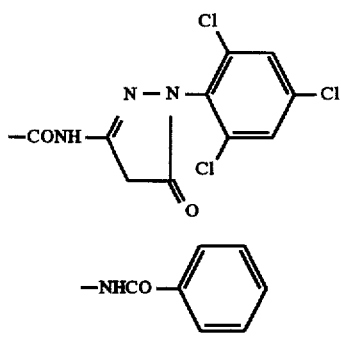

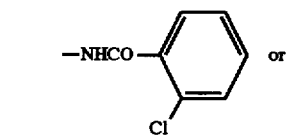

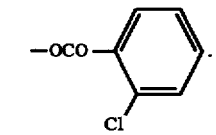 or

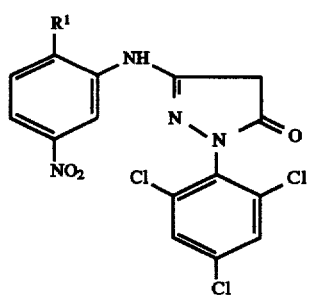

Particularly preferred halonitroaromatic compounds correspond to a compound of the formulae (Id) to (Ig) and the corresponding haloaromatic amines correspond to a compound of the formulae (IId) to (IIg):

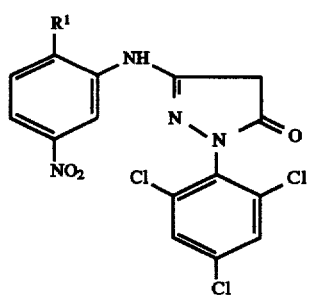 (Id)

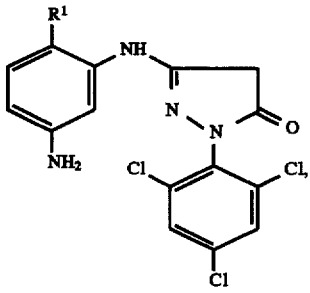 (IId)

where

R¹ is hydrogen or, in particular, chlorine,

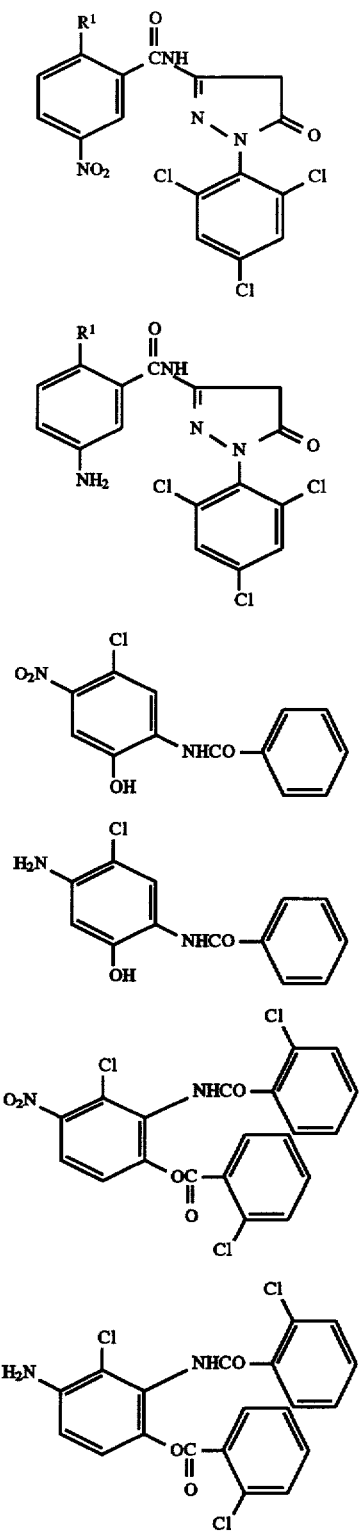

Catalysts used according to the invention are iron-containing Raney nickel catalysts. These catalysts can be prepared by the customary methods for the preparation of Raney catalysts (H. Adkins et al. Org. Syntheses, Coll. Vol. III, 180 (1955)). Customarily, an alloy of about 50% by weight of aluminium and various proportions of nickel and iron is prepared. The major part of the aluminium is leached out of the comminuted alloy by means of hot aqueous sodium hydroxide solution and the catalyst is thus activated. According to the invention, the activated catalysts contain from 1 to 10%, preferably from 3 to 8%, of residual aluminium, from 5 to 30%, preferably from 10 to 20%, of iron and the remainder is nickel (as contents in the dry matter). The amount of catalysts to be used is not critical in principle. However, amounts which are too small lead to hydrogenation times which are too long while excessive amounts are uneconomical. According to the invention, use is made of, for example, from 0.1 to 20% by weight of catalyst dry matter, based on halonitroaromatic compound, preferably from 0.5 to 15% by weight, particularly preferably from 1 to 10% by weight.

Preferably, the preparation of 2-amino-6-chlorophenyl-alkylsulphanes from the corresponding nitro compounds is excepted from the process of the invention, if it is carried out by catalytic hydrogenation without addition of a further sulphur compound in the presence of a solvent.

The process of the invention is generally carried out in an organic solvent. Examples of organic solvents which may be mentioned are aliphatic, water-miscible alcohols having from 1 to 4 carbon atoms, for example methanol, ethanol, 2-methoxyethanol or iso-propanol. Particular preference is given to methanol.

The process of the invention can also be carried out in a mixture of organic solvent and water. It is here advantageous if the water content is less than 50% by weight, preferably less than 10% by weight.

The organic solvent can also be used in admixture with further cosolvents. Such cosolvents are, for example, dimethylformamide, dimethylacetamide and tetrahydrofuran.

It is also possible to use other solvents. Examples which may be mentioned are esters such as methyl or ethyl acetate or ethers such as tetrahydrofuran or diisopropyl ether.

The solubility of sparingly soluble halonitroaromatic compounds which bear an acidic hydrogen atom can be improved by adding a base to the reaction. Preference is given to adding an inorganic base such as alkali metal hydroxide or alkali metal carbonate. Preference is given to the addition of alkali metal hydroxide. The alkali metal hydroxide can be added as an aqueous solution. A further preferred group of bases are the alkali metal alkoxides of lower aliphatic alcohols, if desired as solution in the corresponding alcohol.

However, for carrying out the process of the invention, it is not absolutely necessary for all the halonitroaromatic compound to be completely dissolved. Accordingly, the amount of the bases which may be added can be varied within wide limits in the abovementioned cases. Particularly advantageous is the use of an amount of base of from 50 to 120 mol %, based on the halonitroaromatic compound, preferably from 75 to 110 mol %, particularly preferably from 90 to 110 mol %.

According to the invention, it is possible to neutralize an excess addition of base by addition of a small amount of acid. Suitable acids are, for example, simple mineral acids such as HCl, $H_2SO_4$ or $H_3PO_4$ or simple carboxylic acids such as acetic acid, propionic acid, etc. Preference is given to simple carboxylic acids and phosphoric acid.

The amount of acid to be added is to be selected according to the excess addition of the base such that the remaining amount of base is in a range from 50 to 120 mol %, based on the haloaromatic compound, preferably from 75 to 110 mol %, particularly preferably from 90 to 110 mol %.

The use of bases as described above is particularly preferred when halonitroaromatic compounds of the formula (Id) to (Ig) are used.

The process of the invention is preferably carried out under slightly super-atmospheric hydrogen pressure. A range from 0.1 to 30 bar gauge pressure, preferably from 0.5 to 15 bar gauge pressure, of $H_2$ is advantageous.

The process of the invention is generally carried out at room temperature or at only slightly elevated temperature. A range from 20° to 80° C., preferably from 25° to 60° C., particularly preferably from 25° to 45° C., is advantageous.

Furthermore, it is preferred for the process of the invention to be carried out in a single stage, i.e. without interruption for intermediate metering in of reagents.

The process of the invention can be carried out continuously, semicontinuously or batchwise. An example of an embodiment is as follows: An autoclave is initially charged with the halonitroaromatic compound, the solvent and, if desired, the base, and these are by stirring. The iron-containing Raney nickel catalyst is then added and hydrogen is injected to, for example, 5–10 bar. The exothermic hydrogenation reaction is carried out until the pressure is constant, the autoclave is vented, the catalyst is filtered off and the product is isolated, preferably by precipitation with aqueous acid.

In the process of the invention, it is extremely surprising that the use of the iron-containing Raney nickel catalyst effects such a strong reduction in the dehalogenation compared with the prior art (Raney-Ni).

The amines prepared by the process of the invention, preferably those of the formula II, are used for the preparation of photographic couplers. For this purpose, the amine is reacted with an acid chloride to form an amide. Numerous examples of this are known in the literature (see, for example, U.S. Pat. No. 4 443 536 and the references cited therein in column 1, line 36 to column 2, line 18).

Preferred acid chlorides which may be mentioned are, for example,

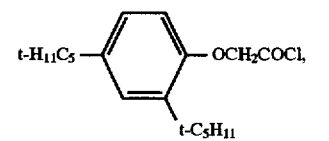
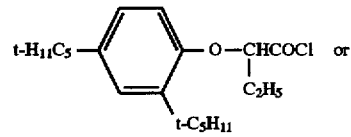
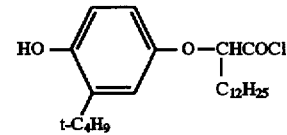

Important photographic couplers which can be prepared from the amines of the formula II prepared according to the invention are, for example, the following:

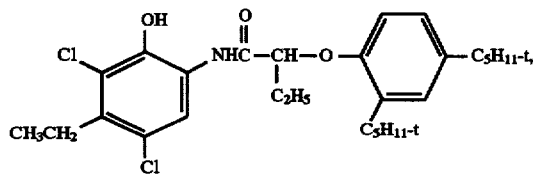
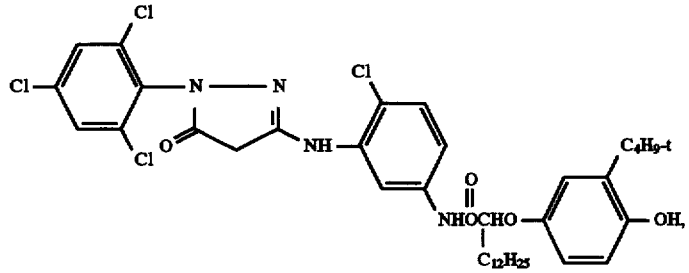
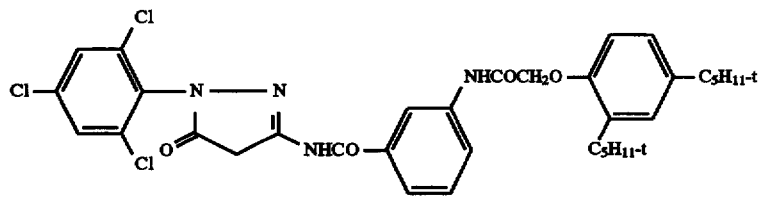

These couplers are preferably used in photographic emulsions or elements. The following examples illustrate the invention, without limiting it thereto.

EXAMPLE 1

A steel autoclave was charged with 100 parts by weight of 3-(5-nitro-2chlorophenylamino)- 1-(2,4,6-trichlorophenyl)-2-pyrazolin-5-one of the formula (Ib), where $R^3$ represents Cl (purity according to HPLC: 95%), 366 parts by weight of technical-grade methanol, 17.5 parts by weight of 50% strength aqueous sodium hydroxide solution and 6.2 parts by weight of 50% strength aqueous Raney nickel/iron of the composition 80.5% of nickel, 14.2% of iron and 5.0% of aluminium, and, after making inert with nitrogen, 5 bar of $H_2$ were introduced at ambient temperature while stirring. An exothermic reaction commenced and the temperature was held at 30° C. by means of cooling. After 7 hours, the autoclave was vented, made inert with nitrogen, the catalyst was filtered off and the clear reaction solution was introduced at from 25° to 30° C. into a mixture of 835 parts by weight of water and 20.2 parts by weight of acetic acid. The resulting suspension was cooled to 0° C. while stirring, and filtered. The solid retained on the filter was washed with 800 parts by weight of water, sucked dry and dried in vacuo at 50° C. This gave 91.0 g of a very pale beige fine powder. HPLC analysis indicated a purity of 99.7%. Dechlorinated compounds were not found in the HPLC (i.e. content <0.1%). The yield was thus 98.5% of theory.

EXAMPLE 2

A steel autoclave was charged with 100 parts by weight of 3-(5-nitro-2-chlorophenylamino)-1-(2,4,6-trichlorophenyl)-2-pyrazolin-5-one of the formula (Ib), where $R^3$=Cl (purity according to HPLC: 95%), 314 parts by weight of methanol, 19.0 parts by weight of 50% strength aqueous sodium hydroxide solution, 1.4 parts by weight of acetic acid and 10.7 parts by weight of 50% strength aqueous Raney nickel/iron of the same composition as in Example 1. After making inert with nitrogen, 5 bar of $H_2$ were introduced while stirring. The temperature was held for 4 hours at a maximum of 30° C., the autoclave was vented, made inert with nitrogen, the catalyst was filtered off and the filtered solution was introduced into a mixture of 716 parts by weight of water and 17.3 parts by weight of acetic acid. After cooling to 0° C., the solid was isolated by filtration and washing with 680 parts by weight of water. This gave, after drying, 105.7 g of a virtually colourless fine powder. HPLC analysis similar to Example 1 gave a purity of 100.0%. Dechlorinated compounds were not found. The yield was thus 98.4% of theory.

EXAMPLE 3

A steel autoclave was charged with 100 parts by weight of 3-(5-nitro-2-chlorophenylamino)-1-(2,4,6-trichlorophenyl)-2-pyrazolin-5-one of the formula (Ib), where $R^3$=Cl, of a lower quality (purity according to HPLC: 76%), 352 parts by weight of methanol, 17.4 parts by weight of 50% strength aqueous sodium hydroxide solution, 1.4 parts by weight of acetic acid and 12.0 parts by weight of 50% strength aqueous Raney nickel/iron of the composition 80.3% of nickel, 13.7% of iron and 5.7% of aluminium. After making inert with nitrogen, 5 bar of $H_2$ were introduced while stirring. The temperature was held for 2 hours 45 minutes at a maximum of 30° C., the autoclave was vented, made inert with nitrogen, the catalyst was filtered off and the clear solution was allowed to run at room temperature into a mixture of 800 parts by weight of water and 15.9 parts by weight of acetic acid. The suspension thus obtained was cooled to 0° C. while stirring. The solid was filtered off with suction, washed with 830 parts by weight of water and dried in vacuo at 50° C. This gave 76.5 g of a virtually colourless fine powder. HPLC analysis similar to Example 1 gave a purity of 99.9%. Dechlorinated compounds were not detected. The yield was thus 99.7% of theory.

EXAMPLE 4

A steel autoclave was charged with 100 parts by weight of 3-(5-nitro-2-chlorophenylamino)-1-(2,4,6-trichlorophenyl)-2-pyrazolin-5-one of the formula (Ib), where $R^3$=Cl (purity according to HPLC: 92%), 440 parts by weight of methanol, 19.0 parts by weight of 50% strength aqueous sodium hydroxide solution, 1.4 parts by weight of acetic acid and 15.0 parts by weight of 50% strength aqueous Raney nickel/iron of the same composition as in Example 3. After making inert with nitrogen, 10 bar of $H_2$ were introduced at a maximum of 32° C. After 2 hours, the autoclave was vented, made inert with nitrogen and the catalyst was filtered off. The clear solution was introduced into a mixture of 870 parts by weight of water and 19.8 parts by weight of acetic acid. After cooling the suspension, the solid was filtered off with suction, washed with 800 parts by weight of water and dried in vacuo at 50° C. This gave 73.6 g of a very pale beige powder. HPLC analysis similar to Example 1 gave a purity of 99.4%. As dechlorinated product, 0.3% of the compound of the formula

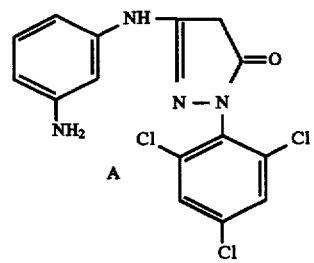

was found.

Other dechlorinated compounds were not detected. This gave a yield of 98.3% of theory.

An otherwise identical reaction but using an iron-free Raney nickel catalyst similar to those of DD-A 159 875, Example 5, gave only 73.1 g of a beige fine powder which contained a very much greater amount of dehalogenated products (see table).

TABLE

| | Composition of the product obtained | | | | |
|---|---|---|---|---|---|
| | Halogen completely retained | Dehalogenated product | | | |
| Catalyst | Product | A | B | C | Σ |
| iron-containing Raney-Ni catalyst (according to the invention) | 99.4% | 0.3% | — | — | 0.3% |
| Raney-Ni | 97.1% | 2.0% | 0.1% | 0.5% | 2.6% |

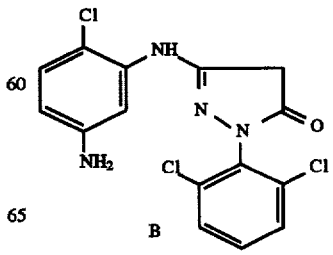

TABLE-continued

Composition of the product obtained

| Catalyst | Halogen completely retained Product | Dehalogenated product | | | |
|---|---|---|---|---|---|
| | | A | B | C | Σ |

C: [structure: 2-chloro-5-amino-phenyl-NH linked to pyrazolone N-N ring with 2,4-dichlorophenyl substituent]

We claim:

1. A process for preparing a haloaromatic amine by catalytic hydrogenation of the corresponding halonitroaromatic compound, wherein iron-containing Raney nickel is used as catalyst and wherein the halonitroaromatic compound corresponds to the formula (I) and the corresponding haloaromatic amine corresponds to the formula (II)

$$A-NO_2 \quad (I)$$
$$A-NH_2, \quad (II)$$

where

A is an aromatic radical to which the $NO_2$ group in formula (I) or the $NH_2$ group in formula (II) is bonded via a ring carbon atom of an aromatic ring and where at least one ring carbon atom of an aromatic ring of the radical A is substituted by at least one halogen atom and wherein the ring A is further substituted with a substituent selected from the group consisting of hydroxy, alkyl, alkoxy, aryloxy, aryl, formyl, alkonoyl, cycloalkanoyl, aroyl, alkanoyloxy, cycloalkanoyloxy, aroyloxy, alkylsulphonyl, cycloalkylsulphonyl, arylsulphonyl, alkylnoylamino, cycloalkylamino, aroylamino, alkylsuphonamido, cycloalkylsulphonamido, arylsuphonamido, alkoxycarbonyl, cycloalkoxycarbonyl, aryloxycarbonyl, carbamoyl, sulphamoyl, alkyl-, aryl- or heterocyclylaminocarbonyl or -carbonylamino and substituted amino.

2. The process according to claim 1, wherein the aromatic radical A bears a substituent selected from the following group $-NHCO-CH_2COC(CH_3)_3$

[structure: −NH−C=CH−CO− with N−N bonded to 2,4,6-trichlorophenyl]

[structure: −CONH−C=CH−CO− with N−N bonded to 2,4,6-trichlorophenyl]

−NHCO−phenyl,

−NHCO−(2-chlorophenyl),

−OH, −CH_3, −CH_2CH_3, −(CH_2)_2CH_3,

−OCO−(2-chlorophenyl).

3. The process according to claim 1, wherein the halonitroaromatic compound of the formula (I) corresponds to the formula Ia, Ib or Ic and the haloaromatic amine of the formula II correspond to the formula IIa, IIb or IIc,

[structure Ia: phenyl with $R^1$, $R^2$, $NO_2$]

[structure IIa: phenyl with $R^1$, $R^2$, $NH_2$]

[structure Ib: phenyl with Cl, $O_2N$, $(R^2)_m$]

[structure IIb: phenyl with Cl, $H_2N$, $(R^2)_m$]

[structure Ic: phenyl with $R^1$, $R^2$, $O_2N$]

-continued

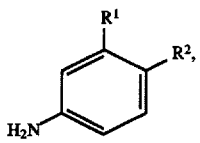
(IIc)

where

R¹ represents hydrogen or chlorine, n represents 1 or 2 and

R² is hydroxy, alkyl, alkoxy, aryloxy, aryl, formyl, alkanoyl, cycloalkanoyl, aroyl, alkanoyloxy, cycloalkanoyloxy, aroyloxy, alkylsulphonyl, cycloalkylsulphonyl, arylsulphonyl, alkanoylamino, cycloalkanoylamino, aroylamino, alkylsulphonamido, cycloalkylsulphonamido, arylsulphonamido, alkoxycarbonyl, cycloalkoxycarbonyl, aryloxycarbonyl, carbamoyl, sulphamoyl, alkyl-, aryl- or heterocyclyl-aminocarbonyl or -carbonylamino and substituted amino.

4. The process according to claim 1, wherein R² represents one of the following radicals:

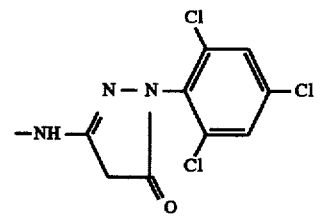

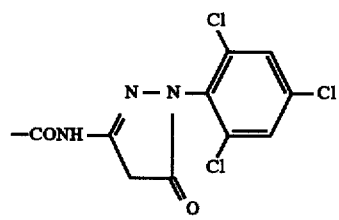

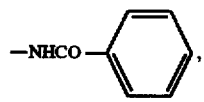

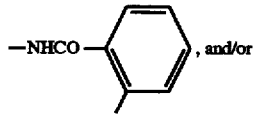,  and/or

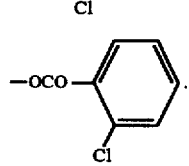.

5. The process according to claim 1, wherein the halonitroaromatic compound corresponds to one of the formulae (Id) to (Ig) and the haloaromatic amine corresponds to one of the formulae (IId) to (IIg)

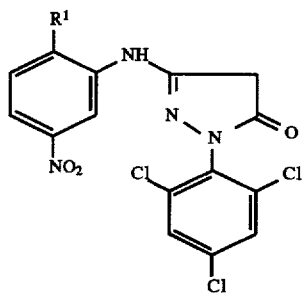
(Id)

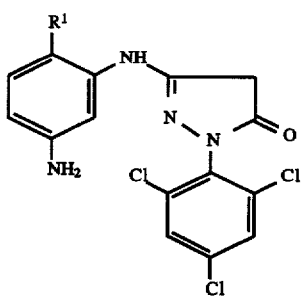
(IId)

where

R¹ is hydrogen,

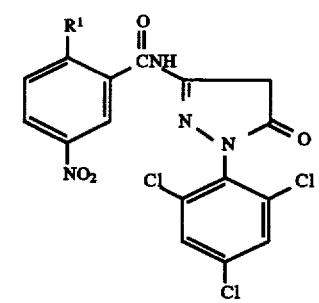
(Ie)

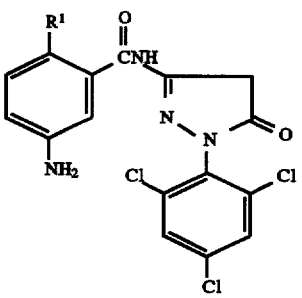
(IIe)

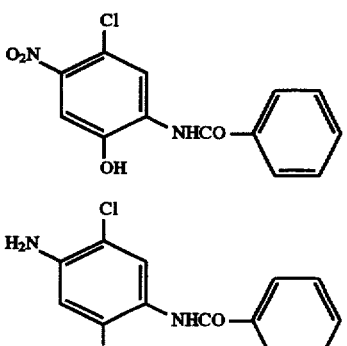
(If)

(IIf)

-continued

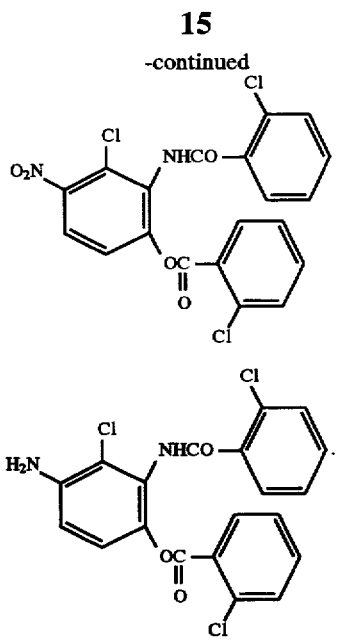

(Ig)

(IIg)

6. The process according to claim 1, wherein the halonitroaromatic compound corresponds to one of the formulae (Id) to (Ig) and the haloaromatic amine corresponds to one of the formulae (IId) to (IIg)

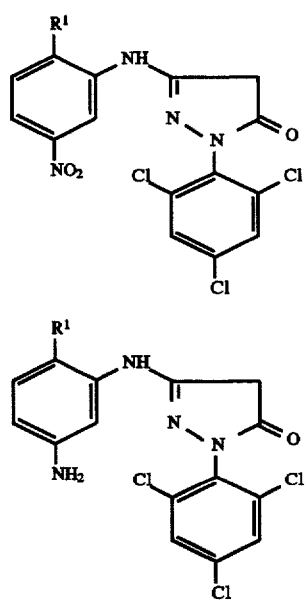

(Id)

(IId)

where
R¹ is chlorine,

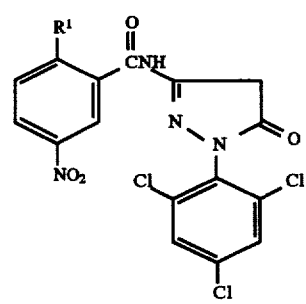

(Ie)

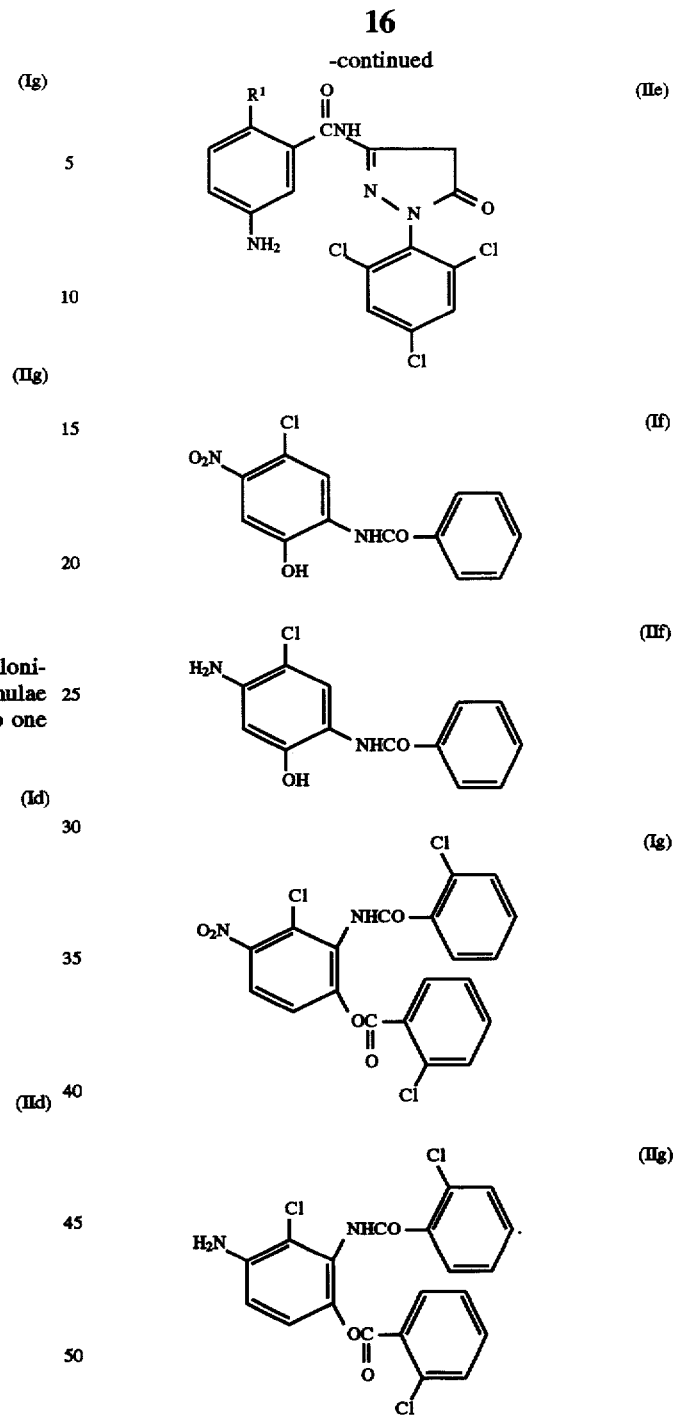

(IIe)

(If)

(IIf)

(Ig)

(IIg)

7. The process according to claim 1, wherein the catalytic hydrogenation is carried out in an aliphatic water-miscible alcohol having from 1 to 4 carbon atoms.

8. The process according to claim 1, wherein an iron-containing Raney nickel catalyst containing from 1 to 10% of aluminium and from 5 to 30% of iron is used.

* * * * *